(12) United States Patent
Stotz et al.

(10) Patent No.: US 12,263,333 B2
(45) Date of Patent: Apr. 1, 2025

(54) STATOR VANE DEVICE FOR GUIDING THE FLOW OF A FLUID FLOWING OUT OF AN OUTLET OPENING OF A VENTRICULAR ASSIST DEVICE, VENTRICULAR ASSIST DEVICE WITH STATOR VANE DEVICE, METHOD FOR OPERATING A STATOR VANE DEVICE AND MANUFACTURING METHOD

(71) Applicant: KARDION GMBH, Stuttgart (DE)

(72) Inventors: Ingo Stotz, Ditzingen (DE); Johannes Bette, Leonberg (DE); Armin Schuelke, Aidlingen (DE); David Minzenmay, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 914 days.

(21) Appl. No.: 17/252,504

(22) PCT Filed: Jun. 21, 2019

(86) PCT No.: PCT/EP2019/066499
§ 371 (c)(1),
(2) Date: Jul. 13, 2021

(87) PCT Pub. No.: WO2019/243588
PCT Pub. Date: Dec. 26, 2019

(65) Prior Publication Data
US 2021/0338999 A1    Nov. 4, 2021

(30) Foreign Application Priority Data
Jun. 21, 2018   (DE) .................... 10 2018 210 058.6

(51) Int. Cl.
*A61M 60/812*  (2021.01)
*A61M 60/178*  (2021.01)
(Continued)

(52) U.S. Cl.
CPC ........ *A61M 60/221* (2021.01); *A61M 60/178* (2021.01); *A61M 60/237* (2021.01);
(Continued)

(58) Field of Classification Search
CPC .............. A61M 60/221; A61M 60/178; A61M 60/237; A61M 60/403; A61M 60/812; A61M 2005/0266; A61M 60/139
See application file for complete search history.

(56) References Cited

U.S. PATENT DOCUMENTS

| 2,254,698 A | 9/1941 | Hansen, Jr. |
| 2,310,923 A | 2/1943 | Bean |

(Continued)

FOREIGN PATENT DOCUMENTS

| AU | 7993698 | 2/1999 |
| AU | 2002308409 | 12/2005 |

(Continued)

OTHER PUBLICATIONS

International Search Report and Written Opinion received in PCT Application No. PCT/EP2019/066499, dated Sep. 25, 2019 in 18 pages.

(Continued)

*Primary Examiner* — Gary Jackson
*Assistant Examiner* — Sebastian X Lukjan
(74) *Attorney, Agent, or Firm* — Knobbe, Martens, Olson & Bear, LLP

(57) ABSTRACT

The invention relates to a stator vane device (105) for guiding the flow of a fluid flowing out of an outlet opening (110) of a heart support system (100). The stator vane device (105) has at least one stator vane (115), which can be connected to the heart support system (100) and arranged in the region of the outlet opening (110). The at least one stator vane (115) is formed such that it can be folded together to (Continued)

take an insertion state of the heart support system (100) and can be unfolded to take a flow guiding state. The at least one stator vane (115) is designed to project radially or obliquely from the heart support system (100) in the flow guiding state.

20 Claims, 3 Drawing Sheets

(51) Int. Cl.
  *A61M 60/221* (2021.01)
  *A61M 60/237* (2021.01)
  *A61M 60/403* (2021.01)
(52) U.S. Cl.
  CPC ........ *A61M 60/403* (2021.01); *A61M 60/812* (2021.01); *A61M 2205/0266* (2013.01)

(56) References Cited

U.S. PATENT DOCUMENTS

| | | |
|---|---|---|
| 3,085,407 A | 4/1963 | Tomlinson |
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,245,622 A | 1/1981 | Hutchins, IV |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,702,430 A | 12/1997 | Larson, Jr. et al. |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,964,694 A | 10/1999 | Siess et al. |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,607,368 B1 | 8/2003 | Ross et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,014,620 B2 | 3/2006 | Kim |
| 7,022,100 B1 | 4/2006 | Aboul-Hosn et al. |
| 7,027,875 B2 | 4/2006 | Siess et al. |
| 7,011,620 B1 | 5/2006 | Siess |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |
| 7,502,648 B2 | 3/2009 | Okubo et al. |
| 7,736,296 B2 | 6/2010 | Siess et al. |
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |

(56) References Cited

U.S. PATENT DOCUMENTS

| | | | |
|---|---|---|---|
| 7,878,967 B1 | 2/2011 | Khanal |
| 7,934,909 B2 | 2/2011 | Jenson |
| 7,914,436 B1 | 3/2011 | Kung |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 * | 4/2014 | Nunez ............... A61M 60/876 600/16 |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,717,833 B2 | 8/2017 | McBride et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,557,475 B2 | 2/2020 | Roehn |

(56) References Cited

U.S. PATENT DOCUMENTS

| | | |
|---|---|---|
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,773,002 B2 | 9/2020 | Siess et al. |
| 10,814,053 B2 | 10/2020 | Throckmorton et al. |
| 10,857,273 B2 | 12/2020 | Hodges et al. |
| 10,864,308 B2 | 12/2020 | Muller et al. |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |

(56) References Cited

U.S. PATENT DOCUMENTS

| | | |
|---|---|---|
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,551 B2 | 10/2023 | Yanai et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,443 B2 | 11/2023 | Hanson et al. |
| 11,813,444 B2 | 11/2023 | Siess et al. |
| 11,819,678 B2 | 11/2023 | Siess et al. |
| 11,826,127 B2 | 11/2023 | Casas |
| 11,833,278 B2 | 12/2023 | Siess et al. |
| 11,833,342 B2 | 12/2023 | Tanner et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| 11,857,743 B2 | 1/2024 | Fantuzzi et al. |
| 11,857,777 B2 | 1/2024 | Earles et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| 11,890,212 B2 | 2/2024 | Gilmartin et al. |
| 11,896,482 B2 | 2/2024 | Delaloye et al. |
| 11,898,642 B2 | 2/2024 | Stanton et al. |
| 11,904,104 B2 | 2/2024 | Jahangir |
| 11,911,579 B2 | 2/2024 | Tanner et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,938,311 B2 | 3/2024 | Corbett et al. |
| 11,944,805 B2 | 4/2024 | Stotz |
| 11,980,385 B2 | 5/2024 | Haselman |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,023,476 B2 | 7/2024 | Tuval et al. |
| 12,023,477 B2 | 7/2024 | Siess |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| 12,076,544 B2 | 9/2024 | Siess et al. |
| 12,076,549 B2 | 9/2024 | Stotz et al. |
| 12,090,314 B2 | 9/2024 | Tuval et al. |
| 12,092,114 B2 | 9/2024 | Siess |
| 12,097,016 B2 | 9/2024 | Goldvasser |
| 12,102,815 B2 | 10/2024 | Dhaliwal et al. |
| 12,107,474 B2 | 10/2024 | Vollmer |
| 12,121,713 B2 | 10/2024 | Calomeni et al. |
| 12,144,936 B2 | 11/2024 | Tao et al. |
| 12,144,976 B2 | 11/2024 | Baumbach et al. |
| 2001/0009645 A1 | 7/2001 | Noda |
| 2001/0041934 A1 | 11/2001 | Yamazaki et al. |
| 2002/0076322 A1 | 6/2002 | Maeda et al. |
| 2002/0082585 A1 | 6/2002 | Carroll et al. |
| 2002/0147495 A1 | 10/2002 | Petroff |
| 2002/0153664 A1 | 10/2002 | Schroeder |
| 2003/0060685 A1* | 3/2003 | Houser ............... A61B 17/0218 600/206 |
| 2003/0091450 A1 | 5/2003 | Davis et al. |
| 2003/0100816 A1 | 5/2003 | Siess |
| 2003/0111800 A1 | 6/2003 | Kreutzer |
| 2003/0139643 A1 | 7/2003 | Smith et al. |
| 2003/0191357 A1 | 10/2003 | Frazier |
| 2003/0199727 A1 | 10/2003 | Burke |
| 2004/0044266 A1 | 3/2004 | Siess et al. |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2005/0254976 A1 | 11/2005 | Carrier et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |

(56) References Cited

U.S. PATENT DOCUMENTS

| | | |
|---|---|---|
| 2008/0306328 A1 | 12/2008 | Ercolani |
| 2009/0004037 A1 | 1/2009 | Ito |
| 2009/0112312 A1 | 4/2009 | Larose et al. |
| 2009/0138080 A1 | 5/2009 | Siess et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0268017 A1 | 10/2010 | Siess |
| 2010/0298625 A1 | 11/2010 | Reichenbach et al. |
| 2011/0172505 A1 | 7/2011 | Kim |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0029265 A1 | 2/2012 | LaRose |
| 2012/0035645 A1 | 2/2012 | Gross |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0245404 A1 | 9/2012 | Smith |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0053623 A1* | 2/2013 | Evans ............... A61M 60/585 600/16 |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0030122 A1 | 1/2014 | Ozaki |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141842 A1 | 5/2015 | Spanier et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0067395 A1 | 3/2016 | Jimenez et al. |
| 2016/0144089 A1 | 5/2016 | Woo et al. |
| 2016/0144166 A1 | 5/2016 | Decréet al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0256620 A1 | 9/2016 | Scheckel et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0043074 A1 | 2/2017 | Siess |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-Hardt et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0232169 A1 | 8/2017 | Muller |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311421 A1 | 11/2018 | Tuseth |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0333059 A1 | 11/2018 | Casas |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |

(56) References Cited

U.S. PATENT DOCUMENTS

| | | |
|---|---|---|
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0211847 A1 | 7/2019 | Walsh et al. |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0261633 A1 | 8/2020 | Spanier |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0323742 A1 | 10/2022 | Grauwinkel et al. |
| 2022/0407403 A1 | 12/2022 | Vogt et al. |
| 2023/0001178 A1 | 1/2023 | Corbett et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0075277 A1 | 3/2024 | Schellenberg |
| 2024/0102475 A1 | 3/2024 | Schuelke et al. |
| 2024/0198084 A1 | 6/2024 | Stotz |
| 2024/0245902 A1 | 7/2024 | Schlebusch et al. |
| 2024/0269459 A1 | 8/2024 | Schellenberg et al. |
| 2024/0277998 A1 | 8/2024 | Vogt et al. |
| 2024/0285935 A1 | 8/2024 | Popov et al. |
| 2024/0335651 A1 | 10/2024 | Mitze et al. |
| 2024/0399135 A1 | 12/2024 | Stotz et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 292 432 | 5/1998 |
| CA | 2 664 835 | 2/2008 |
| CA | 2 796 357 | 10/2011 |
| CA | 2 947 984 | 11/2022 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 101128168 | 2/2008 |
| CN | 201150675 | 11/2008 |
| CN | 101677812 | 3/2010 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |

(56) References Cited

FOREIGN PATENT DOCUMENTS

| | | |
|---|---|---|
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 27 07 951 | 9/1977 |
| DE | 26 24 058 | 12/1977 |
| DE | 3 545 214 | 7/1986 |
| DE | 41 05 278 | 8/1992 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 039 658 | 3/2011 |
| DE | 20 2009 018 416 | 8/2011 |
| DE | 10 2010 041 995 | 4/2012 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 119 451 | 6/2019 |
| EP | 3 528 865 | 8/2019 |
| EP | 3 536 360 | 9/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 687 625 | 8/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 740 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 3 794 720 | 3/2021 |
| EP | 2 344 218 | 4/2021 |
| EP | 3 436 104 | 4/2021 |
| EP | 3 749 383 | 4/2021 |
| EP | 3 821 938 | 5/2021 |
| EP | 3 131 615 | 6/2021 |

(56) References Cited

FOREIGN PATENT DOCUMENTS

| | | |
|---|---|---|
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 930 785 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 2 961 984 | 9/2023 |
| EP | 3 352 808 | 9/2023 |
| EP | 3 554 576 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 782 695 | 3/2024 |
| EP | 3 854 448 | 3/2024 |
| EP | 4 271 461 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 3 854 444 | 9/2024 |
| EP | 3 534 985 | 10/2024 |
| EP | 3 793 674 | 10/2024 |
| EP | 3 893 957 | 10/2024 |
| EP | 3 914 334 | 10/2024 |
| EP | 4 034 221 | 11/2024 |
| EP | 4 087 641 | 11/2024 |
| FR | 1458525 | 3/1966 |
| FR | 2 768 056 | 3/1999 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515374 | 9/2001 |
| JP | 2001-515375 | 9/2001 |
| JP | 2003-019197 | 1/2003 |
| JP | 2003-525438 | 8/2003 |
| JP | 2004-019468 | 1/2004 |
| JP | 2004-278375 | 10/2004 |
| JP | 2005-028137 | 2/2005 |

(56) References Cited

FOREIGN PATENT DOCUMENTS

| | | |
|---|---|---|
| JP | 2005-507039 | 3/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 | 1/2017 |
| JP | 6267625 | 1/2018 |
| JP | 2018-057878 | 4/2018 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/036927 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |

(56) References Cited

FOREIGN PATENT DOCUMENTS

| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |
| WO | WO 2023/230157 | 11/2023 |
| WO | WO 2024/243154 | 11/2024 |

OTHER PUBLICATIONS

International Preliminary Report on Patentability received in PCT Application No. PCT/EP2019/066499, dated Apr. 2, 2020 in 6 pages.

"ABMD—Taking a Closer Look at Impella ECP as the Pivotal Trial Gets Underway", Guggenheim, Press Release, Mar. 29, 2022, pp. 4.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Escudeiro et al., "Tribological behavior of uncoated and DLC-coated CoCr and Ti-alloys in contact with UHMWPE and PEEK counterbodies;" Tribology International, vol. 89, 2015, pp. 97-104.

Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.

Neale, Michael J., "The Tribology Handbook;" 1999, Butterworth-Heinemann, Second Edition, pp. 582.

Park et al., "A Novel Electrical Potential Sensing Method for in Vitro Stent Fracture Monitoring and Detection", Jan. 1, 2011, vol. 21, No. 4, pp. 213-222.

Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.

Ai, X. (2013). Radial Bearings. In: Wang, Q.J., Chung, YW. (eds) Encyclopedia of Tribology. Springer, Boston, MA https://doi.org/10.1007/978-0-387-92897-5_334, accessed Oct. 18, 2024, pp. 4.

"Edwards SAPIEN 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien 3/doc-0045537b%20-%20certitude.pdf.

GGB by Timken Bearings FAQ; "What is a Slide Bearing ?; " https://www.ggbearings.com/en/why-choose-ggb/faq/bearings-faq/what-slide-bearing; accessed Oct. 10, 2024, pp. 1.

Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg 7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.

Gopinath, Divya, "A System for Impedance Characterization of Coronary Stents", University of Strathclyde Engineering, Thesis, Aug. 2015, pp. 77.

McMaster-Carr Online Catalog, "Bearings search results;" https://www.mcmaster.com/products/bearings/; accessed Oct. 18, 2024, pp. 5.

McMaster-Carr Online Catalog, "Slide Bearings search results;" https://www.mcmaster.com/products/slide-bearings/; accessed Oct. 18, 2024, pp. 21.

RBCBearings.com, "RBC Bearings Incorporated—Products;" https://www.rbcbearings.com/Products; accessed Oct. 18, 2024, pp. 2.

SKF.com; "Products: Bearings;" https://www.skf.com/us/products/bearings; accessed Oct. 18, 2024, pp. 8.

Wikipedia, "Plain Bearing," https://en.wikipedia.org/wiki/Plain_bearing; accessed Oct. 18, 2024, pp. 10.

\* cited by examiner

STATOR VANE DEVICE FOR GUIDING THE FLOW OF A FLUID FLOWING OUT OF AN OUTLET OPENING OF A VENTRICULAR ASSIST DEVICE, VENTRICULAR ASSIST DEVICE WITH STATOR VANE DEVICE, METHOD FOR OPERATING A STATOR VANE DEVICE AND MANUFACTURING METHOD

BACKGROUND

Field

The invention relates to a stator vane device for guiding the flow of a fluid flowing out of an outlet opening of a heart support system. The invention also relates to a heart support system with a stator vane device, to a method for operating a stator vane device, and to a manufacturing method for manufacturing a stator vane device. The invention moreover relates to a computer program and to a machine-readable storage medium on which the computer program is stored.

Description of the Related Art

For cardiovascular support of patients having heart failure, systems, so-called ventricular assist devices (VADs), which take over part or all of the pumping function of the heart can be used. These systems can be subdivided into temporary systems for short-term heart support, e.g., to bridge the time until a suitable donor heart is available and can be implanted, and permanent systems for long-term retention on or in the patient. One component of such a system can be a pump for pumping a blood stream, typically a centrifugal pump (turbo pump), which can be driven by an integrated electric motor and can produce the required blood flow by means of an impeller. In this case, the pump can be implanted at different locations: The pump can be sutured to the heart from the outside by means of an invasive surgery, a sternotomy, or the pump can be placed transfemorally or transaortally into the aorta and completely or partially into the ventricle in a minimally invasive manner by means of a catheter. In the case of a pump that can be introduced in a minimally invasive manner, the maximum possible outer diameter of the pump may be limited to allow transfemoral or transaortic insertion of the pump, which is why the pump may have an axial design. The pump can pump the blood stream from the ventricle into the aorta and deliver it there. This can lead to total pressure losses and thus to a reduced pump efficiency due to a cross-sectional jump of the pump in relation to the aorta. Furthermore, a velocity component can be applied to the blood flow by the impeller in the circumferential direction, i.e., an angular momentum or a swirl component, wherein the energy contained in this swirl component is without effect and thus not usable for pressure build-up.

SUMMARY

The object of the invention is to influence the flow of a fluid in which a heart support system is located. It is in particular an object of the invention to influence the flow of the blood in a blood vessel in which a heart support system is arranged. The object of the invention is also to optimize the efficiency of a pump in a heart support system.

These objects are achieved by the stator vane device specified herein for guiding the flow of a fluid flowing out of an outlet opening of a heart support system and the heart support system specified herein with a stator vane device. Advantageous embodiments and further developments described herein also relate to a method for operating a stator vane device and to a manufacturing method for manufacturing a stator vane device.

The invention is based on the knowledge that it is possible by means of a suitable stator vane device to change the flow behavior of a fluid flowing out of an outlet opening of a heart support system. By means of the stator vane device, an angular momentum in the flow of the fluid applied by an impeller of a pump of the heart support system can advantageously be reduced. In addition, the angular momentum can be partially converted into pressure energy, which can advantageously increase the efficiency of the pump.

Presented is a stator vane device for guiding the flow of a fluid flowing out of an outlet opening of a heart support system. The stator vane device has at least one stator vane. The at least one stator vane can be connected to the heart support system and arranged in the region of the outlet opening. In addition, the at least one stator vane is formed such that it can be folded together to take an insertion state of the heart support system and can be unfolded to take a flow guiding state. The at least one stator vane is designed to project radially or obliquely from the heart support system in the flow guiding state.

The stator vane device can, for example, have a fixing device for fixing the stator vane device to the heart support system, or the stator vane device can, for example, be formed as part of a pump housing section of the heart support system. The at least one stator vane can, for example, have a blade-shaped guide surface. The term "guiding the flow" can be understood to mean, for example, adjusting a flow behavior, e.g., by steering the fluid along a surface, e.g., in the form of the at least one stator vane. The heart support system can, for example, be a heart pump, such as a right ventricular support system, a left ventricular support system, a biventricular support system, or a vascular or valve prosthesis. For minimally invasive transfemoral or transaortic insertion, the heart support system can, for example, have an elongated, cylindrical shape with an outer diameter of 5 to 8 millimeters. The outlet opening can, for example, be arranged in the region of an impeller of a blood pump of the heart support system. The outlet opening can, for example, be arranged in a section of a pump housing of the heart support system and be cut or punched out of said section. The fluid can, for example, be blood that can be pumped by means of the heart support system. The insertion state of the heart support system can, for example, describe a state into which the heart support system can be transferred for insertion into a blood vessel; for this purpose, the heart support system can, for example, have a cylindrical shape with an outer diameter that is below the diameter of a human aorta. In the insertion state, the stator vane device can, for example, be foldable together axially of a longitudinal axis of the heart support system. By unfolding the at least one stator vane, the stator vane device can, for example, be transferred from the insertion state into the flow guiding state when the heart support system is implanted at the destination and ready for operation. For this purpose, the stator vane can, for example, open to project radially or obliquely from the heart support system in the flow guiding state. In the flow guiding state, the stator vane can also open to project obliquely, e.g., at a certain spatially variable angle to the radius. In this case, the inclination angle of the stator vane can have a radial and a tangential component.

According to one embodiment, the stator vane device can be formed at least partially from a shape memory material.

For this purpose, the at least one stator vane can, for example, be made of a shape memory material or the stator vane can have a support structure which is formed from the shape memory material and dilapidated with another material, such as silicone or polyurethane. The shape memory material can, for example, be a shape memory polymer or a shape memory alloy, such as nitinol. It is furthermore also possible for the entire stator vane device to be made of a shape memory alloy, e.g., nitinol. Due to its shape memory properties, the use of a shape memory material, such as nitinol, allows particularly simple realization of the insertion state and the unfolding during the transition into the flow guiding state. The use of nitinol as a shape memory material is advantageous since the nitinol material is a proven material in medicine, in particular in the field of cardiovascular medicine, e.g., for heart valve prostheses, stents, and vascular prostheses, because due to its shape memory property, it is possible to deliver even complex structures in a small installation space to the destination and to place them there.

The stator vane device according to one embodiment can furthermore be formed at least partially from a biocompatible material. The biocompatible material can be a material in which components of human or animal tissue remain unchanged, in particular non-degenerated, when in contact with this biocompatible material. For example, the biocompatible material can be nitinol or a biocompatible silicone or polyurethane. The forming of at least a part of the stator vane device from a biocompatible material is advantageous with regard to the use of the stator vane device as a device that can, for example, be implanted into a human body in connection with the heart support system.

According to one embodiment, the at least one stator vane can be formed such that it abuts laminarly on the heart support system in the insertion state. For this purpose, the stator vane can be foldable in the direction of the heart support system in the insertion state, for example. In the insertion state, the stator vane can, for example, abut on a pump housing section. This allows a compact design and is also advantageous in order to be able to, for example, introduce the stator vane device with the heart support system into an insertion device, such as a catheter, in order to allow the minimally invasive insertion of the stator vane device or of the heart support system connected to the stator vane device.

In addition, the at least one stator vane can be formed in order to be partially insertable into the outlet opening in the insertion state. For this purpose, the stator vane can, for example, be formed to correspond to the outlet opening at least in sections. If the stator vane device is formed, for example, as a part of a housing section of a heart support system, the housing section can also be cut from a tube, wherein the shape of the at least one stator vane for forming the outlet opening can also be cut into the tube, wherein the stator vane can be folded away from the housing section to open the outlet opening. This embodiment advantageously allows a compact design, which is particularly advantageous with regard to a design suitable for minimally invasive introduction.

According to one embodiment, the stator vane device can also have at least one further stator vane, which can be connected to the heart support system and arranged in the region of the outlet opening. The at least one further stator vane can be formed such that it can be folded together to take an insertion state of the heart support system and can be unfolded to take a flow guiding state. The at least one further stator vane can be designed to project radially or obliquely from the heart support system in the flow guiding state. The at least one further stator vane can be arranged opposite the stator vane, for example. The stator vane device can also have a plurality of stator vanes, which can be equidistantly arranged circumferentially around the heart support system. Depending on the shape of the stator vane and of the outlet opening, the design of the at least one further stator vane can be advantageous with regard to guiding the flow of the outflowing fluid, as a result of which the efficiency of the pump of the heart support system can be increased.

According to one embodiment, the stator vane device can also have a sleeve that is movable with respect to the stator vane and is formed to enclose the stator vane in the insertion state and release the stator vane in order to initiate the transition into the flow guiding state. The sleeve can be a mounting device for maintaining the insertion state, e.g., a tube that encloses the stator vane in the insertion state and thereby presses it against the heart support system. The sleeve can, for example, be formed to be cylindrical and designed such that the stator vane device with the sleeve in the insertion state can be inserted into a commercially available catheter. The sleeve can, for example, be used to hold down the stator vane in the folded-together state and to thereby additionally stabilize it in the insertion state even if the stator vane device is, for example, completely or partially made of a shape memory material.

According to one embodiment, the stator vane device can be detachably connectable or connected to a pump housing section of the heart support system. For this purpose, the stator vane device can have, for example, a fixing device or connecting device for connecting the stator vane device or the at least one stator vane to the pump housing section of the heart support system in a form-fitting manner, which fixing device or connecting device can be detached mechanically or as a result of the forming from a shape memory material. This embodiment is cost-saving in order to be able to replace the stator vane device independently of the pump housing, for example, or to be able to change a position of the stator vane with respect to the pump housing section.

A heart support system with an embodiment of the aforementioned stator vane device is also presented. In particular, the stator vane device can be designed as part of a pump housing of the heart support system, which is advantageous with respect to the design.

With this approach, a method for operating an embodiment of the aforementioned stator vane device is also presented. The method has a step of unfolding the at least one stator vane during the transition from the insertion state into the flow guiding state, wherein the at least one stator vane projects radially or obliquely from the heart support system in the flow guiding state.

A manufacturing method for manufacturing an embodiment of the aforementioned stator vane device comprises a step of providing the stator vane device with at least one stator vane. The at least one stator vane can be connected to a heart support system and arranged in the region of an outlet opening of the heart support system. The at least one stator vane is formed such that it can be folded together to take an insertion state of the heart support system and can be unfolded to take a flow guiding state. The at least one stator vane can project radially or obliquely from the heart support system in the flow guiding state, wherein the stator vane device is in particular designed as part of a pump housing of the heart support system.

This method can, for example, be implemented in software or hardware or in a mixed form of software and hardware in a control device, for example.

A computer program product or computer program having program code which can be stored on a machine-readable carrier or storage medium, such as a semiconductor memory, a hard drive memory, or optical memory, and is used to carry out, implement, and/or control the steps of the methods according to one of the embodiments described above is also advantageous, in particular if the program product or program is executed on a computer or a device.

BRIEF DESCRIPTION OF THE DRAWINGS

Exemplary embodiments of the approach presented here are shown in the drawings and explained in more detail in the following description. The drawings show.

DETAILED DESCRIPTION

In the following description of favorable exemplary embodiments of the present invention, the same or similar reference signs are used for the elements that are shown in the various figures and have a similar effect, wherein a repeated description of these elements is omitted.

Figure 1:
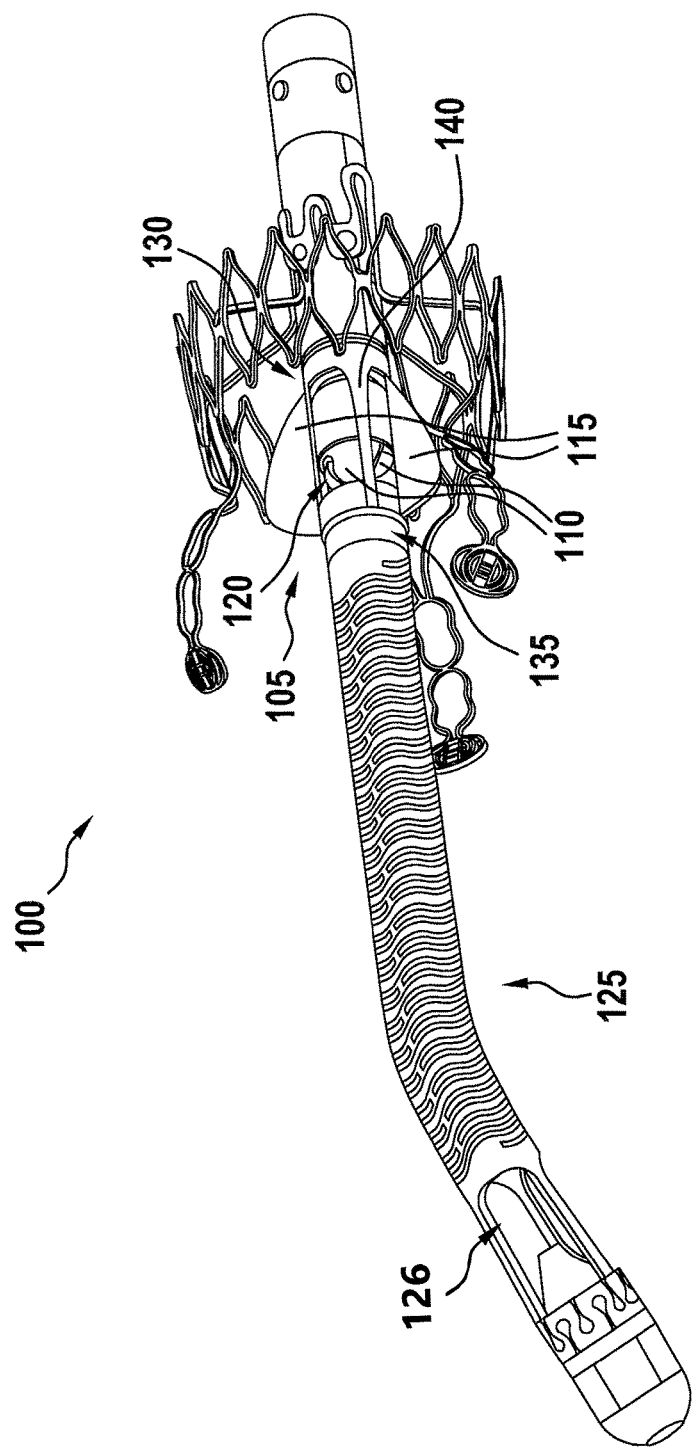
FIG. 1 a schematic illustration of a heart support system with a stator vane device for guiding the flow of a fluid flowing out of an outlet opening of the heart support system according to an exemplary embodiment.

FIG. 1 shows a schematic illustration of a heart support system 100 with a stator vane device 105 for guiding the flow of a fluid flowing out of an outlet opening 110 of the heart support system 100 according to an exemplary embodiment. A perspective view of the heart support system 100 is shown. As heart support system 100, a left ventricular heart support system for an aortic valve position is shown by way of example.

The stator vane device 105 has at least one stator vane 115. The at least one stator vane 115 can be connected to the heart support system 100. In addition, the at least one stator vane 115 can be arranged in the region of the outlet opening 110 of the heart support system 100. The at least one stator vane 115 is formed such that it can be folded together to take an insertion state of the heart support system 100 and can be unfolded to take a flow guiding state. In the flow guiding state, the at least one stator vane 115 projects radially or obliquely from the heart support system 100. The stator vane device 105 is shown here by way of example in the flow guiding state; accordingly, the stator vane 115 is unfolded and projects radially from the heart support system 100. Shown here by way of example are two stator vanes 115 which are arranged opposite one another in the unfolded state. Alternatively, the stator vane 115 can also project obliquely from the heart support system 100 at an acute or obtuse angle to the radius of the heart support system 100. In this case, an inclination angle of the stator vane 115 can have a radial and a tangential component. According to the exemplary embodiment shown here, a plane of the stator vane 115 extends in the direction of a longitudinal extension axis of the heart support system 100.

The heart support system 100 has a cylindrical, elongated structure with a substantially constant outer diameter and rounded, tapered ends for easy positioning by means of a catheter in a blood vessel, e.g., the aorta. The elongated axial design shown here allows transfemoral implantation of the heart support system 100, wherein the outer diameter of the heart support system 100 is limited in the inserted state by the diameter of the femoral artery in the region of the implantation site. In the following, the heart support system 100 is also referred to as pump 100 in short.

The pump 100 has an impeller 120, which is formed as an axial-flow impeller with respect to a longitudinal axis of the pump 100. The impeller 120 is arranged in a pump housing section 135 of the heart support system 100 between an inlet tube 125 with an inlet opening 126 for introducing the fluid to be conveyed and a section, comprising a drive device 130, of the heart support system 100. The impeller 120 can be rotated about an axis of rotation 122 parallel to the longitudinal direction of the pump housing section 135. The impeller 120 is enclosed by the pump housing section 135, which has a lateral surface, arranged coaxially to the axis of rotation 122 of the impeller 120, with the outlet opening 110, which lateral surface is interrupted by the outlet opening 110. The fluid, e.g., blood, to be conveyed by the heart support system 100 can be introduced through the inlet opening 126 of the inlet tube 125 and discharged through the outlet opening 110 installed on the circumference of the pump housing section 135 in order to be returned to the aorta in the implanted state of the heart support system 100. The pump housing section 135 has here, by way of example, two window-like outlet openings 110.

According to one exemplary embodiment, the stator vane device 105 is formed at least partially from a shape memory material and, additionally or alternatively, at least partially from a biocompatible material. In addition, according to one exemplary embodiment, the stator vane device 105 can be detachably connectable or connected to the pump housing section 135 of the heart support system.

According to one exemplary embodiment, the heart support system 100 has the stator vane device 105 as part of a pump housing of the heart support system 100, e.g., as part of the pump housing section 135.

Figure 2:
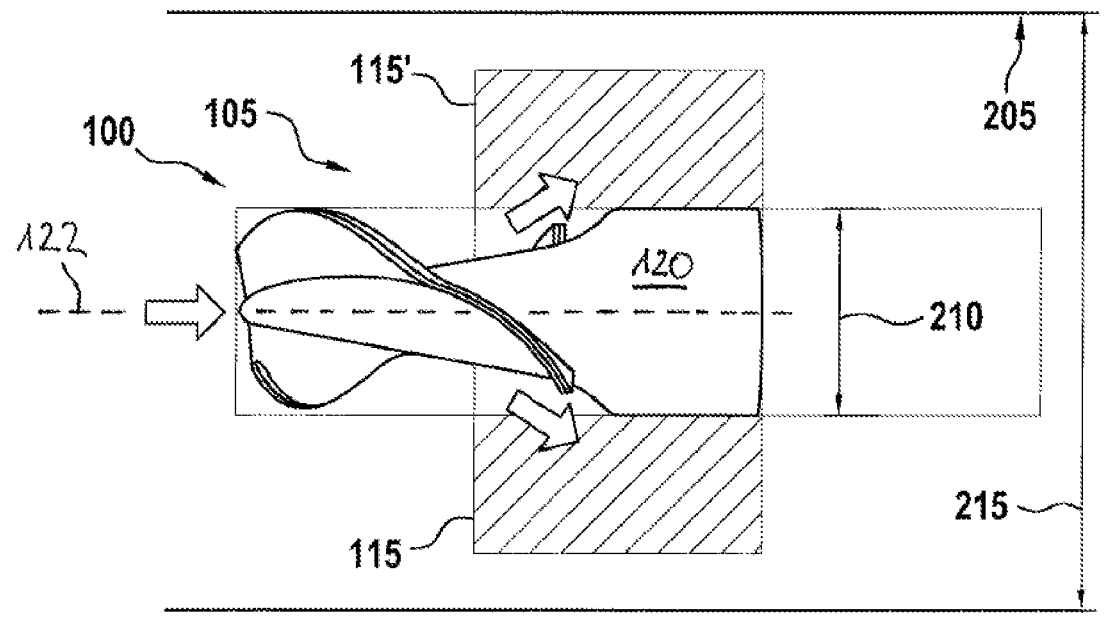
FIG. 2 a schematic illustration of a stator vane device for guiding the flow of a fluid flowing out of an outlet opening of a heart support system in the flow guiding state according to an exemplary embodiment.

For minimally invasive insertion, the pump 100 has a significantly smaller outer diameter than the aorta, into which the blood flows out in the implanted state during operation of the heart support system 100, as shown schematically with reference to the following FIG. 2. Without the stator vane device 105, due to the large, abrupt cross-sectional jump, this results in permanent total pressure losses and thus in reduced pump efficiency. Furthermore, a velocity component is applied to the fluid by the impeller 120 in the circumferential direction, i.e., a swirl component. The energy contained in this swirl component is without effect and thus lost. By means of an exemplary embodiment of the stator vane device 105 shown here, the aforementioned swirl in the flow is reduced by the at least one stator vane 115 and at least partially converted into pressure energy in order to increase the efficiency of the pump 100.

The at least one stator vane 115 projects in a flow guiding state from the lateral surface of the pump housing section 135. In the flow guiding state, the at least one stator vane 115 can project from the lateral surface of the pump housing section 135 in a direction which has a direction component parallel and a direction component perpendicular to a radial direction with respect to the axis of rotation 122 of the impeller 120. The at least one stator vane 115 can be parallel to the axis of rotation 122 of the impeller 120. However, the at least one stator vane 115 can in principle also extend obliquely to the axis of rotation 122 of the impeller 120.

The guiding of the flow achieved by means of the unfolded stator vane 115 in the flow guiding state of the stator vane device 105 allows the increased efficiency of the pump 100. In this case, the blood is fed from the ventricle through the inlet tube 125 to the active pump part, inter alia to the impeller 120. The impeller 120 is partially enclosed on the outside by the pump housing section 135, which has the outlet opening 110 and is, by way of example, cylindrical here. According to the exemplary embodiment shown here, the pump housing section 135 also has the bars 140, also called struts. The at least one stator vane 115 is arranged in the region of the outlet opening 110 or the bars 140. The at least one stator vane 115 is flexible, foldable, and unfoldable. The stator vane 115 can be folded together to take the insertion state, and the stator vane 115 can be unfolded to take the flow guiding state, as shown with reference to the following FIGS. 2 and 3.

For taking the insertion state and the flow guiding state, the stator vane device 105 and, additionally or alternatively, the entire pump housing section 135 with the stator vane device 105 is, according to one exemplary embodiment, formed from nitinol, a biocompatible shape memory alloy, in order to fold the at least one stator vane 115 to a small diameter.

According to one exemplary embodiment, the stator vane device 105 comprises a sleeve as a mounting device in order to be maintained in this folded state at this small diameter by an additional mounting device, e.g., by a tube. The sleeve is movable with respect to the stator vane 115 and is formed in order to enclose the stator vane 115 in the insertion state and to release the stator vane 115 in order to initiate the transition into the flow guiding state. If the stator vane is formed from nitinol according to one exemplary embodiment, the at least one stator vane 115 unfolds to the desired unfolded state, i.e., to the flow guiding state, by the influence of body heat after implantation of the heart support system 100 and removal of the additional mounting device. Optionally, the entire stator vane 115 is in this case not formed from nitinol but consists only partially of nitinol in the form of a support structure which is made of nitinol and filled with another material, such as a silicone or polyurethane.

FIG. 2 shows a schematic illustration of a stator vane device 105 for guiding the flow of a fluid flowing out of an outlet opening of a heart support system 100 in the flow guiding state according to an exemplary embodiment. In accordance with the flow guiding state, the stator vane 115 is shown in the unfolded state and projects radially from the heart support system 100, i.e., it projects radially from the lateral surface of the pump housing section 135 with respect to the axis of rotation 122 of the impeller 120 that is parallel to the longitudinal direction of the pump housing section 135. The heart support system 100 shown here and the stator vane device 105 shown here resemble or correspond to the heart support system and the stator vane device from FIG. 1 described above. By way of example, the heart support system 100 with the stator vane device 105 is arranged here in the aorta 205.

According to the exemplary embodiment shown here, the stator vane device 105 comprises the stator vane 115 and at least one further stator vane 115', which can be connected to the heart support system 100 and arranged in the region of the outlet opening and is formed such that it can be folded together to take the insertion state of the heart support system 100 and can be unfolded to take the flow guiding state. In the flow guiding state shown here, the at least one further stator vane 115', like the stator vane 115, projects radially from the heart support system 100, i.e., it projects radially from the lateral surface of the pump housing section 135 that is coaxial to the axis of rotation 122 of the impeller 120.

The heart support system 100 has a significantly smaller outer diameter than the blood vessel in which it can be arranged, i.e., the aorta 205. This is shown here by the marking 210, which marks the outer diameter of the heart support system, and the marking 215, which marks the diameter of the aorta. When blood flows out of the outlet opening of the heart support system 100 into the aorta 205, permanent total pressure losses, and thus reduced pump efficiency, occur without the stator vane device 105 due to the large, abrupt cross-sectional jump; furthermore, a velocity component in the circumferential direction, i.e., a swirl component, is applied to the fluid, the blood, by the impeller. The energy contained in this swirl component is without effect and thus lost. By means of the stator vane 115 and optionally the further stator vane 115' in the flow guiding state shown here, the described swirl is reduced and converted into pressure energy, which increases the efficiency of the pump.

Figure 3:
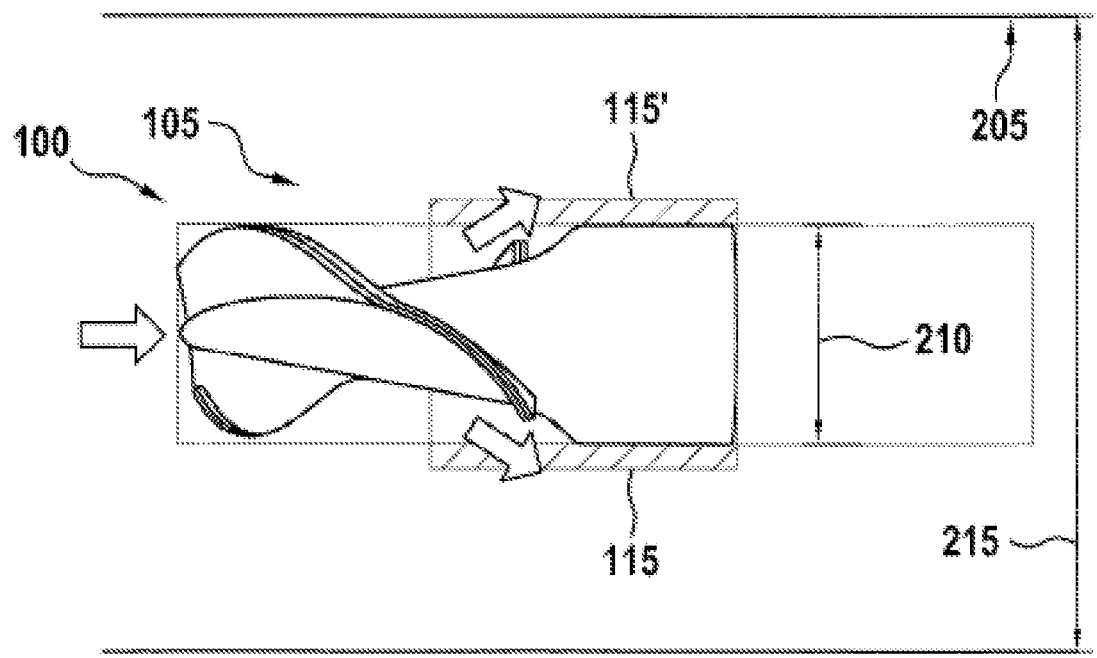
FIG. 3 a schematic illustration of a stator vane device for guiding the flow of a fluid flowing out of an outlet opening of a heart support system in the insertion state according to an exemplary embodiment.

FIG. 3 shows a schematic illustration of a stator vane device 105 for guiding the flow of a fluid flowing out of an outlet opening of a heart support system 100 in the insertion state according to an exemplary embodiment. The insertion state is shown as a further situation of the stator vane device 105 and the heart support system 100 described with reference to the previous figures.

In the insertion state, the heart support system 100 and the stator vane device 105 have a significantly smaller outer diameter than the diameter of the aorta 205, as shown by the markings 210 and 215. This is advantageous for the minimally invasive insertion of the heart support system 100 and the stator vane device 105.

Optionally, the at least one stator vane 115 is formed such that it abuts laminarly in the insertion state, as shown here by way of example by the further stator vane 115'. The stator vane 115' abuts on the pump housing of the heart support system 100 and does not significantly increase the outer diameter 210 of the heart support system 100 in the folded-together state. According to the exemplary embodiment shown here, the at least one stator vane 115 is additionally formed such that it can be partially inserted into the outlet opening in the insertion state, as shown by way of example by the stator vane 115. The described shapes of the stator vane 115 and of the further stator vane 115' offer the advantage that they nestle closely against the pump housing of the heart support system 100 in the folded state or, additionally or alternatively, at least partially lay in the outlet opening and thus allow minimally invasive implantation. The stator vane 115 and the further stator vane 115' are optionally designed as part of the pump housing of the heart support system 100.

Figure 4:
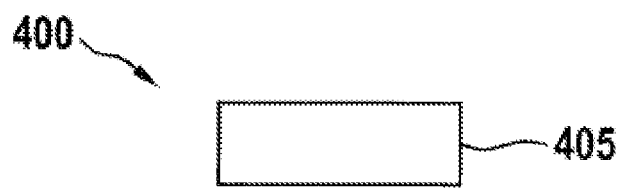
FIG. 4 a flow diagram of a method for operating a stator vane device according to an exemplary embodiment.

FIG. 4 shows a flow diagram of a method 400 for operating a stator vane device according to an exemplary embodiment. With this method 400, an exemplary embodiment of the aforementioned stator vane device is operated. The method 400 has at least one step 405 of unfolding. In step 405 of unfolding, the at least one stator vane is unfolded during the transition from the insertion state into the flow guiding state. In the flow guiding state, the at least one stator vane projects radially or obliquely from the heart support system.

Figure 5:
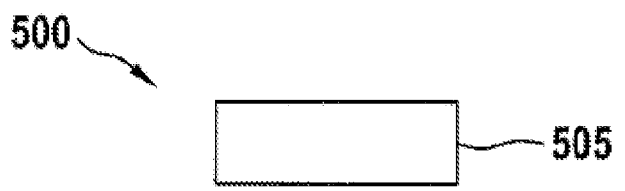
FIG. 5 a flow diagram of a manufacturing method for operating a stator vane device according to an exemplary embodiment.

FIG. 5 shows a flow diagram of a manufacturing method 500 for manufacturing a stator vane device according to an exemplary embodiment. With this manufacturing method 500, an exemplary embodiment of the aforementioned stator vane device is manufactured. The method 500 has at least one step 505 of providing. Provided in step 505 of providing is a stator vane device with at least one stator vane, which can be connected to a heart support system and arranged in the region of an outlet opening of the heart support system and is formed such that it can be folded together to take an insertion state of the heart support system and can be unfolded to take a flow guiding state, wherein the at least one stator vane projects radially or obliquely from the heart support system in the flow guiding state. The stator vane device is in particular provided as part of a pump housing of the heart support system.

If an exemplary embodiment includes an "and/or" conjunction between a first feature and a second feature, this should be read to mean that the exemplary embodiment according to one embodiment has both the first feature and the second feature and according to another embodiment has either only the first feature or only the second feature.

In summary, the following preferred features of the invention should in particular be noted:

The invention relates to a stator vane device 105 for guiding the flow of a fluid flowing out of an outlet opening 110 of a heart support system (100). The stator vane device 105 has at least one stator vane 115, which can be connected to the heart support system 100 and arranged in the region of the outlet opening 110. The at least one stator vane 115 is formed such that it can be folded together to take an insertion state of the heart support system 100 and can be unfolded to take a flow guiding state. The at least one stator vane 115 is designed to project radially or obliquely from the heart support system 100 in the flow guiding state.

In particular, the invention can have the following aspects:

1. Stator vane device (105) for guiding the flow of a fluid flowing out of an outlet opening (110) of a heart support system (100), wherein the stator vane device (105) has the following features:

at least one stator vane (115), which can be connected to the heart support system (100) and arranged in the region of the outlet opening (110) and is formed such that it can be folded together to take an insertion state of the heart support system (100) and can be unfolded to take a flow guiding state, wherein the at least one stator vane (115) is designed to project radially or obliquely from the heart support system (100) in the flow guiding state.

2. Stator vane device (105) according to Aspect 1, wherein the stator vane device (105) is formed at least partially from a shape memory material.

3. Stator vane device (105) according to one of the preceding aspects, wherein the stator vane device (105) is formed at least partially from a biocompatible material.

4. Stator vane device (105) according to one of the preceding aspects, wherein the at least one stator vane (115) is formed such that it abuts laminarly on the heart support system (100) in the insertion state.

5. Stator vane device (105) according to one of the preceding aspects, wherein the at least one stator vane (115) is formed such that it can be partially inserted into the outlet opening (110) in the insertion state.

6. Stator vane device (105) according to one of the preceding aspects, with at least one further stator vane (115'), which can be connected to the heart support system (100) and arranged in the region of the outlet opening (110) and is formed such that it can be folded together to take the insertion state of the heart support system (100) and can be unfolded to take the flow guiding state, wherein the at least one further stator vane (115') is designed to project radially from the heart support system (100) in the flow guiding state.

7. Stator vane device (105) according to one of the preceding aspects, with a sleeve that is movable with respect to the stator vane (115) and is formed to enclose the stator vane (115) in the insertion state and release the stator vane (115) in order to initiate the transition into the flow guiding state.

8. Stator vane device (105) according to one of the preceding aspects, wherein the stator vane device (105) is detachably connectable or connected to a pump housing section (135) of the heart support system (100).

9. Heart support system (100) with a stator vane device (105) according to one of the preceding Aspects 1 to 8, wherein the stator vane device (105) is in particular designed as part of a pump housing of the heart support system (100).

10. Method (400) for operating a stator vane device (105) according to one of the preceding Aspects 1 to 8, wherein the method (400) has at least the following step:

unfolding (405) the at least one stator vane (115) during the transition from the insertion state into the flow guiding state, wherein the at least one stator vane (115) projects radially or obliquely from the heart support system (100) in the flow guiding state.

11. Manufacturing method (500) for manufacturing a stator vane device (105) according to one of the preceding Aspects 1 to 8, wherein the manufacturing method (500) has at least the following step:

providing (505) a stator vane device (105) with at least one stator vane (115), which can be connected to a heart support system (100) and arranged in the region of an outlet opening (110) of the heart support system (100) and is formed such that it can be folded together to take an insertion state of the heart support system (100) and can be unfolded to take a flow guiding state, wherein the at least one stator vane (115) is designed to project radially or obliquely from the heart support system (100) in the flow guiding state, wherein the stator vane device (105) is in particular designed as part of a pump housing of the heart support system (100).

12. Computer program configured to execute and/or control the method (400) according to Aspect 10 and/or the manufacturing method (500) according to Aspect 11.

13. Machine-readable storage medium on which the computer program according to Aspect 12 is stored.

The invention claimed is:

1. A heart support system, comprising:
an inlet tube extending in a longitudinal direction, the inlet tube comprising an inlet opening positioned in a distal portion of the inlet tube and configured to receive blood into the heart support system;
a pump housing connected to a proximal end of the inlet tube and extending proximally in the longitudinal direction and downstream from the inlet tube, the pump housing comprising:
a lateral surface comprising at least one outlet opening configured to receive discharged blood therethrough from the pump housing; and a stator vane device arranged in the region of the at least one outlet opening, the stator vane device comprising at least one stator vane configured to unfold from a folded-in state to a flow guiding state after the inlet tube and pump housing section are inserted into a blood vessel using a catheter, wherein the at least one stator vane is configured to project radially or obliquely from the lateral surface of the pump housing in the flow guiding state;

an impeller positioned at least partially lateral to the at least one outlet opening within the pump housing and having an axis of rotation parallel to the longitudinal direction of the pump housing; and a drive device positioned on a side of the impeller opposite the inlet tube and configured to drive the impeller.

2. The heart support system according to claim 1, further comprising a sleeve configured to be movable with respect to the at least one stator vane, wherein the sleeve is configured to enclose the at least one stator vane in the folded-in state and release the at least one stator vane to initiate the unfolding of the at least one stator vane from the folded-in state to the flow guiding state.

3. The heart support system according to claim 1, wherein the inlet tube comprises a rounded, tapered end configured to be received in a blood vessel.

4. The heart support system according to claim 1, wherein the at least one stator vane comprises an edge extending parallel to the axis of rotation of the impeller.

5. The heart support system according to claim 1, wherein the at least one stator vane extends obliquely to the axis of rotation of the impeller.

6. The heart support system according to claim 1, wherein the at least one stator vane is configured to project in the flow guiding state from the lateral surface of the pump housing section in a direction that has a directional component parallel and a directional component perpendicular to a radial direction with respect to the axis of rotation of the impeller.

7. The heart support system according to claim 1, wherein the stator vane device is formed at least partially from a shape memory material.

8. The heart support system according to claim 1, wherein the stator vane device is formed at least partially from a biocompatible material.

9. The heart support system according to claim 1, wherein the at least one stator vane is configured to abut the lateral surface of the pump housing in the folded-in state.

10. The heart support system according to claim 1, wherein the at least one stator vane is partially inserted into the at least one outlet opening in the folded-in state.

11. The heart support system according to claim 1, wherein the at least one stator vane comprises a plurality of stator vanes.

12. The heart support system according to claim 11, wherein the plurality of stator vanes are positioned equidistantly around the circumference of the pump housing.

13. The heart support system according to claim 1, wherein the at least one outlet opening comprises an outlet window defined by one or more bars.

14. The heart support system according to claim 1, wherein the at least one outlet opening comprises a plurality of outlet openings, each of the plurality of outlet openings comprising an outlet window, wherein each outlet window is separated from at least one adjacent outlet window by a bar.

15. The heart support system according to claim 1, wherein the at least one stator vane is partially inserted into the at least one outlet opening in the folded-in state.

16. A method comprising:
providing a heart pump system comprising:
an inlet tube, wherein the inlet tube extends in a longitudinal direction, wherein the inlet tube comprises an inlet opening positioned in a distal portion of the inlet tube and configured to receive blood into the heart support system;

a pump housing, wherein the pump housing is connected to a proximal end of the inlet tube and extends proximally in the longitudinal direction and downstream from the inlet tube, wherein the pump housing comprises:
a lateral surface comprising at least one outlet opening configured to receive discharged blood therethrough from the pump housing; and
a stator vane device arranged in the region of the at least one outlet opening, the stator vane device comprising at least one stator vane;

an impeller positioned at least partially lateral to the at least one outlet opening within the pump housing and having an axis of rotation parallel to the longitudinal direction of the pump housing; and a drive device positioned on a side of the impeller opposite the inlet tube and configured to drive the impeller;

inserting the inlet tube and the pump housing of the heart pump system into a blood vessel using a catheter; and unfolding the at least one stator vane from a folded-in state to a flow guiding state, wherein the at least one stator vane is configured to project radially or obliquely from the lateral surface of the pump housing in the flow guiding state.

17. The method according to claim 16, further comprising moving a sleeve relative to the at least one stator vane to uncover the at least one stator vane and initiate the unfolding of the at least one stator vane from the folded-in state to the flow guiding state.

18. The method according to claim 16, wherein the inlet tube comprises a rounded, tapered end configured to be received in a blood vessel.

19. The method according to claim 16, wherein the stator vane device is formed at least partially from a shape memory material.

20. The method according to claim 16, wherein the stator vane device is formed at least partially from a biocompatible material.

* * * * *